US00PP23615P3

(12) United States Plant Patent
Blom

(10) Patent No.: US PP23,615 P3
(45) Date of Patent: May 21, 2013

(54) *CHRYSANTHEMUM* PLANT NAMED 'ZANMUTANG'

(50) Latin Name: ***Chrysanthemum×morifolium* Ramat.**
Varietal Denomination: Zanmutang

(75) Inventor: Wilhelmus Bernardus Blom, Leimuiden (NL)

(73) Assignee: Chrysanthemum Breeders Association Research B.V., Valkenburg Z-H (NL)

( * ) Notice: Subject to any disclaimer, the term of this patent is extended or adjusted under 35 U.S.C. 154(b) by 94 days.

(21) Appl. No.: 13/200,328

(22) Filed: Sep. 23, 2011

(65) Prior Publication Data
US 2013/0081161 P1 Mar. 28, 2013

(51) Int. Cl.
*A01H 5/00* (2006.01)

(52) U.S. Cl.
USPC ..... Plt./295

(58) Field of Classification Search ..... Plt./295
See application file for complete search history.

*Primary Examiner* — Annette Para
(74) *Attorney, Agent, or Firm* — Steptoe & Johnson LLP

(57) ABSTRACT

A *chrysanthemum* plant named 'Zanmutang' characterized by its small sized blooms with yellow ray florets and prolific branching; natural season flower date September 20 (week 38) blooming for a period of 4 weeks.

3 Drawing Sheets

Botanical designation: *Chrysanthemum×morifolium* Ramat.

Cultivar denomination: 'Zanmutang'.

RELATED CULTIVARS

This new plant cultivar 'Zanmutang' is related to 'Zanmudande' (U.S. Plant patent application Ser. No. 13/200,327), a sibling obtained from the same cross with parent plants.

BACKGROUND OF THE INVENTION

The present invention relates to a new and distinct cultivar of *Chrysanthemum* plant, botanically known as *Chrysanthemum×morifolium* Ramat., commercially known as a garden mum, and hereinafter referred to by the cultivar denomination 'Zanmutang'. 'Zanmutang' is a product of a breeding and selection program for outdoor pot mums (garden mums) which had the objective of creating new cultivars with a double type inflorescence, a natural season flower date around September 20 (week 38), blooming for a period of 4 weeks. 'Zanmutang' is a seedling resulting from a cross of the female parent id 21570 with the male parent id 23262. Both parents are unpatented plants. Plants of the new cultivar 'Zanmutang' differ from plants of the female parent in the following characteristics. (1) Plant vigor and (2) Natural season flower date. (1) Plants of the seedling are more vigorous than plants of the female parent. (2). Plants of the seedling flower earlier in season than plants of the female parent.

Plants of the new cultivar 'Zanmutang' differ from plants of the male parent in the following characteristics. (1) Plant vigor and (2) Natural season flower date. (1) Plants of the seedling are less vigorous than plants of the male parent. (2). Plants of the seedling flower earlier in season than plants of the male parent.

The new and distinct cultivar was discovered and selected as a flowering plant by Wilhelmus Bernardus Blom on a cultivated field in Rijsenhout, The Netherlands in 2005. The first act of asexual production of 'Zanmutang' was accomplished when vegetative cuttings from the initial selection in 2005 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *Chrysanthemum* is shown in the accompanying drawings, the color being as nearly true as possible with color photographs of this type.

DESCRIPTION OF THE INVENTION

Figure 1:
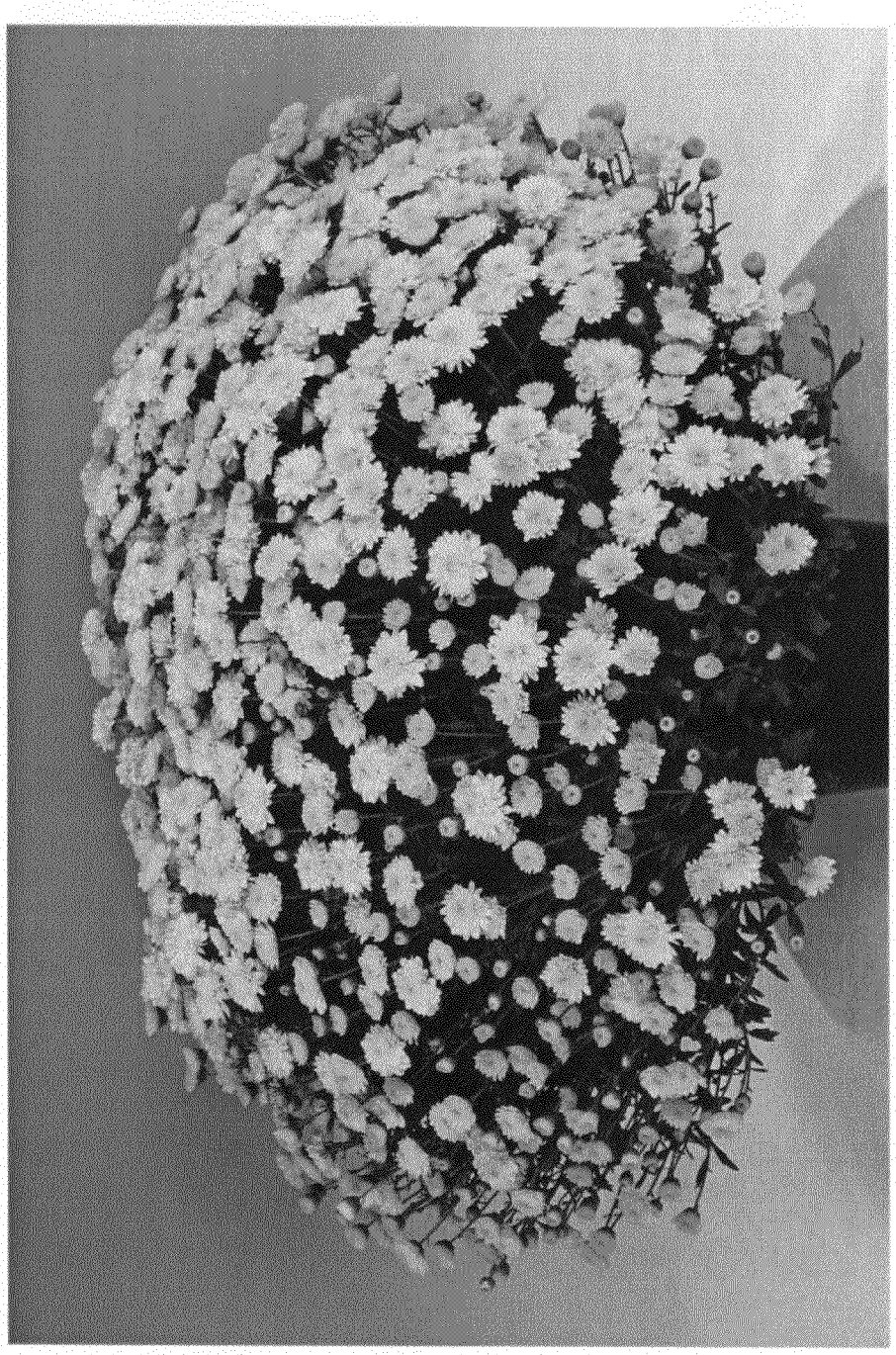
FIG. 1 shows a plant of the cultivar in full bloom.
Figure 2:
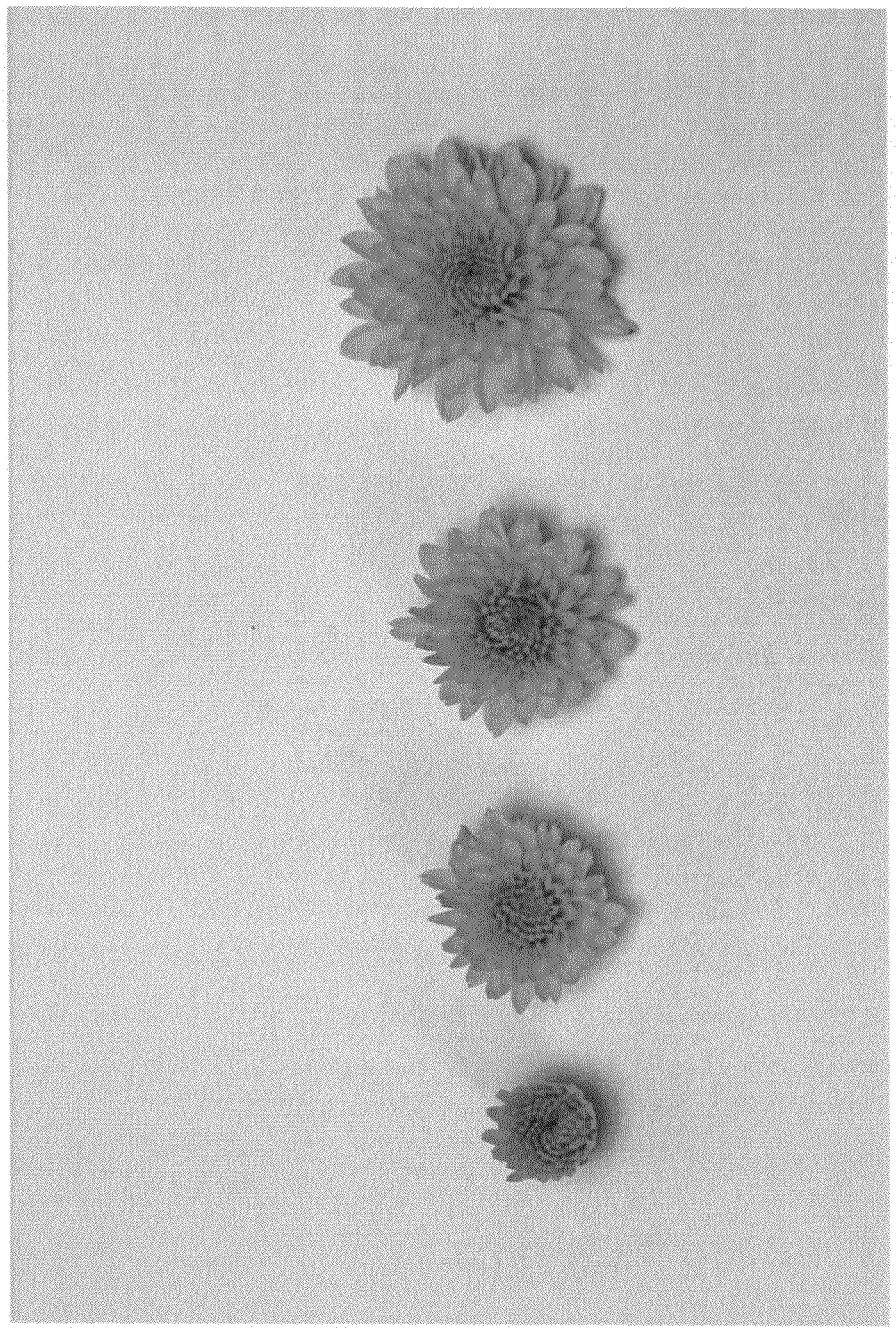
FIG. 2 shows the various stages of bloom of the new cultivar.
Figure 3:
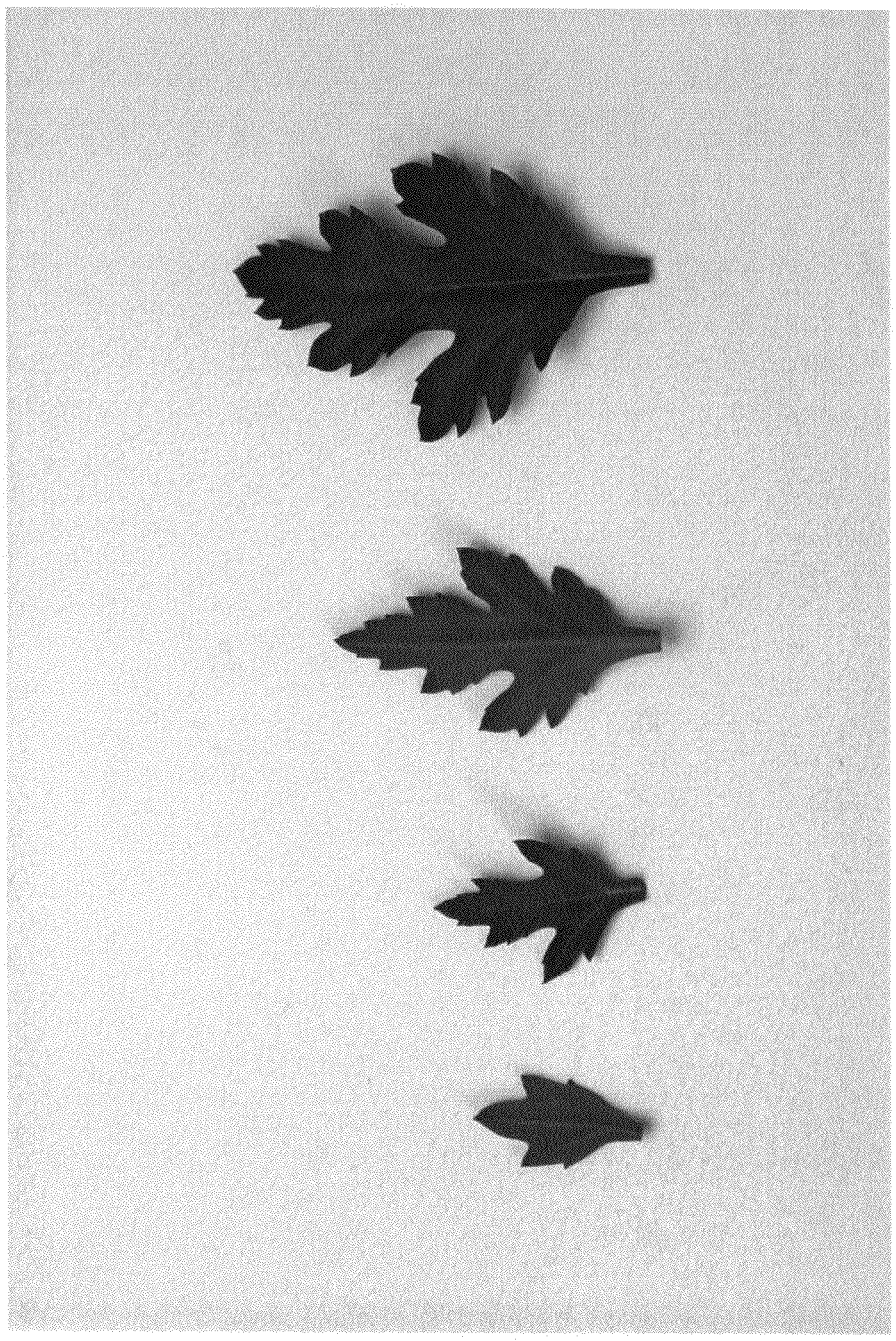
FIG. 3 shows the various stages of foliage of the new cultivar.

The observations and measurements were gathered from plants grown out door in Rijsenhout, The Netherlands under natural day length and temperature and planted in week 23 in 2005. The natural blooming date of this crop was September 20 (week 38). The average height of the plants was 35 cm. No growth retardants were used. No tests were done on disease or insect resistance or susceptibility. No tests were done on cold or drought tolerance. This new variety produces small sized blooms with yellow ray florets blooming for a period of 4 weeks.

From the cultivars known to inventor the most similar existing cultivar in comparison to 'Zanmutang' is 'Zanmusundance' (U.S. Plant Pat. No. 21,163.). When 'Zanmusundance' and 'Zanmutang' are being compared the following difference are noticed: (1) Inflorescence shape. And (2) Number ray florets. (1) The decorative type inflorescences of 'Zanmutang' are more round shaped, while those of 'Zanmusundance' are more flat. (2). The number of ray florets is higher in 'Zanmutang' than in 'Zanmusundance'.

The following is a description of the plant and characteristics that distinguish 'Zanmutang' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

| Detailed Botanical Description | |
|---|---|
| **Bud** | |
| Size | Small; cross-section 5 mm, height 4 mm |
| Shape | Round |
| Texture | Pubescent |
| Outside Color | Greyed-green 191A |
| **Phyllaries** | |
| Number | 20, arranged in 3 rows |
| Shape | Elliptic |
| Apex | Acute |
| Base | Truncate |
| Margin | Entire |
| Color | Upper surface: Green 137C<br>Lower surface: Green 137D |
| Length and width | 4 mm; 2 mm |
| Texture | Pubescent |
| **Inflorescences** | |
| Type | Double |
| Height | 1.2-1.3 cm |
| Diameter | 3 cm |
| Peduncle length | 5.6-6 cm |
| Peduncle color | Green 137C |
| Peduncle diameter | 1.5 mm |
| Peduncle texture | Pubescent |
| Number per branch | Approx. 5 inflorescences |
| Duration of flowering | 4 weeks |
| Seeds | Produced in small quantities, ovate, Greyed-brown 199A, length 1.5 mm, diameter 0.5 mm |
| Fragrance | Faint chrysanthemum odor |
| **Color** | |
| Center of inflorescence | Immature stage: Yellow 13B<br>Mature stage: Yellow 7A |
| Color of upper surface of the ray-florets | Yellow 13C |
| Color of the lower surface of the ray-florets | Yellow 11C |
| Tonality from Distance | A garden mum with yellow blooms |
| Color of the ray-florets after aging of the plant | Yellow 13c |
| **Ray florets** | |
| Texture | Upper and lower surface smooth |
| Number | 230-240 |
| Shape | Elliptic |
| Apex | Dentate |
| Base | Attentuate |
| Cross-section | Flat |
| Longitudinal axis of majority | Straight |
| Length of corolla tube | 4 mm |
| Ray-floret margin | Entire |
| Ray-floret length | 1.2-2 cm |
| Ray-floret width | 3-4 mm |
| Ratio length/width | High |
| **Disc florets** | |
| Disc diameter in mature inflorescences | 2-4 mm |
| Distribution of disc florets | Scarce |
| Shape | Tubular |
| Color | Yellow-green 145C at base to Green Yellow 1D at apex |
| Length | 3.8 mm |
| Diameter | 2.5 mm |

TABLE 1-continued

| Detailed Botanical Description | |
|---|---|
| **Receptacle** | |
| Color | Yellow-green 145D |
| Shape | Conical raised |
| Height | 4 mm |
| Diameter | 3 mm |
| **Reproductive Organs** | |
| Androecium | Present on only disc florets |
| Stamen length | 3 mm |
| Stamen color | Yellow-green 144A |
| Anther color | Yellow 3A |
| Pollen | Present |
| Pollen color | Yellow 13A |
| Gynoecium | Present on both ray and disc florets |
| Style color | Yellow-green 154C |
| Style Length | 3 mm |
| Stigma color | Yellow 7A |
| Stigma Width | 1 mm |
| Ovary | Enclosed in calyx |
| **Plant** | |
| Form | Grown as a spray type pot mum, outdoor raised and mounded |
| Growth habit | Spherical shape |
| Growth rate | Medium |
| Height | 35 cm |
| Width | 50-55 cm |
| Stem Color | Greyed-brown 199A |
| Stem Strength | Strong |
| Stem Brittleness | Brittle |
| Stem Anthocyanin Coloration | Not observed |
| Internode length | 2-2.5 cm |
| Length of lateral branch | From top to bottom 18-20 cm |
| Lateral branch color | Green 137 C |
| Lateral branch, attachment | Brittle |
| Lateral branch diameter | 2 mm |
| Branching (average number of lateral branches) | Prolific with 7 breaks after pinching |
| Natural season blooming date | September 20 (week 38) |
| **Foliage** | |
| Leaf color | Upper side: Green 139A to 139B<br>Lower side: Green 137D |
| Color midvein | Upper side: Yellow-green 147D<br>Lower side: Yellow-green 148D |
| Size | Small; length 1.5-3 cm, width 1-2.5 cm |
| Quantity (number per lateral branch) | 17-19 |
| Shape | Elliptic |
| Texture upper side | Sparsely pubescent |
| Texture under side | Pubescent |
| Venation arrangement | Palmate |
| Shape of the margin | Smooth to serrated |
| Shape of Base of Sinus Between Lateral Lobes | Rounded |
| Margin of Sinus Between Lateral Lobes | Diverging |
| Shape of Base | Attenuate |
| Apex | Mucronulate |
| Petiole length | 3-4 mm |
| Petiole diameter | 1 mm |
| Petiole color | Yellow-green 147D |

TABLE 2

| Differences with the comparison varieties | | |
|---|---|---|
| | 'Zanmutang' | 'Zanmusundance' |
| Inflorescence height | 1.2-1.5 cm | 0.5 cm |
| Number ray florets | 230-240 | Approx. 140 |

I claim:

1. A new and distinct *Chrysanthemum* plant named 'Zanmutang' as described and illustrated.

* * * * *